(12) United States Patent
Mizutani et al.

(10) Patent No.: US 6,548,731 B2
(45) Date of Patent: Apr. 15, 2003

(54) ABSORBENT ARTICLE WITH HYDROPHILIC AGGREGATES IN TOPSHEET

(75) Inventors: Satoshi Mizutani, Kagawa (JP); Makoto Suekane, Kagawa (JP); Junichi Noguchi, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/883,970

(22) Filed: Jun. 19, 2001

(65) Prior Publication Data

US 2001/0053899 A1 Dec. 20, 2001

(30) Foreign Application Priority Data

Jun. 19, 2000 (JP) .................................... 2000-182858

(51) Int. Cl.[7] ................................................ A61F 13/15
(52) U.S. Cl. ...................... 604/365; 604/367; 604/370; 604/374; 604/378; 604/384
(58) Field of Search ...................... 604/385.01, 383, 604/378, 380, 365, 367, 370, 375, 384

(56) References Cited

U.S. PATENT DOCUMENTS

| | | | | |
|---|---|---|---|---|
| 3,122,140 A | * | 2/1964 | Crowe, Jr. ............... | 128/296 |
| 3,371,667 A | * | 3/1968 | Morse ...................... | 128/290 |
| 3,838,694 A | | 10/1974 | Mesek ...................... | 128/287 |
| 3,938,522 A | * | 2/1976 | Repke ....................... | 128/287 |
| 3,965,904 A | * | 6/1976 | Mesek et al. ............. | 604/366 |
| 4,223,677 A | * | 9/1980 | Anderson ................. | 128/287 |
| 4,775,579 A | * | 10/1988 | Hagy et al. .............. | 427/284 |
| 5,383,870 A | * | 1/1995 | Takai et al. .............. | 604/378 |
| 5,591,149 A | * | 1/1997 | Cree et al. ............... | 604/378 |
| 5,821,179 A | | 10/1998 | Masaki et al. ........... | 442/375 |

FOREIGN PATENT DOCUMENTS

| | | | |
|---|---|---|---|
| EP | 0358031 | 3/1990 | ............ A61F/13/15 |
| EP | 0570016 | 11/1993 | ............ A61F/13/15 |
| EP | 0815819 | 6/1996 | ............ A61F/13/15 |
| JP | 54-102095 | 8/1979 | |
| JP | 56065630 | 6/1981 | ............ B01J/20/26 |
| JP | 08-04289 | 1/1996 | |
| WO | 91/14414 | 10/1991 | ............ A61F/13/15 |

* cited by examiner

Primary Examiner—Weilun Lo
Assistant Examiner—Jacqueline F Stephens
(74) Attorney, Agent, or Firm—Darby & Darby

(57) ABSTRACT

Disclosed is an absorbent article including a topsheet, a backsheet and an absorbent core positioned between the topsheet and the backsheet. The topsheet contains hydrophobic fibers and hydrophilic fibers shorter than the hydrophobic fibers. The hydrophobic fibers are thermally bonded to each other. At least a part of the hydrophilic fibers form aggregates that disperse in the sheet. At least a part of the hydrophilic fibers that form the aggregates are bonded to the surfaces of the hydrophobic fibers.

8 Claims, 6 Drawing Sheets

ABSORBENT ARTICLE WITH HYDROPHILIC AGGREGATES IN TOPSHEET

BACKGROUND OF THE INVENTION

1. Field of the Invention

The present invention relates to an absorbent article capable of absorbing and retaining body exudates such as typically menses, in particular, to such an absorbent article having a topsheet that rapidly passes a large amount of liquid therethrough so as to keep its surface still in a dry condition while absorbing a small amount of liquid but not having a wet feel.

2. Description of the Related Art

Heretofore, various types of absorbent articles such as sanitary napkins, urine pads and disposable diapers have been developed. These absorbent articles comprise a liquid-impermeable back layer (backsheet), a liquid-permeable top layer (topsheet) and an absorbent layer (absorbent core) positioned between the two sheets.

Regarding its structure, for example, the liquid-permeable top layer comprises a thermal-bonded nonwoven fabric of hydrophobic fibers having a relatively large porosity, or comprises a nonwoven fabric mainly of cellulosic fibers in its entirety as in Japanese Patent Laid-Open No. 24289/1996. In addition, Japanese Patent Laid-Open No. 10209/1979 discloses a top layer that comprises a nonwoven fabric of from 70 to 85% by weight of hydrophobic synthetic fibers and from 15 to 30% by weight of hydrophilic fibers.

When the aforementioned absorbent article that comprises a top layer of hydrophobic fibers has received a large amount of liquid, the liquid applied to its top layer is immediately brought into contact with an absorbent layer positioned therebelow, and the liquid within the top layer is drawn by the absorbent layer owing to the hydrophilic capillary action of the absorbent layer. In this stage, since the fibers constituting the top layer is poorly resistant to the liquid penetration (movement) through them, almost all the liquid having been applied to the top layer is rapidly drawn by the absorbent layer, not remaining in the top layer, and the surface of the top layer is therefore readily kept in a dry condition.

However, when the top layer has received a small amount of liquid or the sweat of a wearer, such a small amount of liquid will adhere to the fibers constituting the top layer but is hardly brought into contact with the absorbent layer. In that condition, therefore, the drawing force of the absorbent layer does not act on the small amount of liquid, and, as a result, the small amount of liquid often remains in the space between the hydrophobic fibers constituting the top layer. In addition, since the hydrophilic capillary action of the top layer of hydrophobic fibers is poor, the small amount of liquid remaining in the top layer often returns to the skin of a wearer. Accordingly, the top layer is liable to give a wet feel to a wearer and cause skin roughness.

In order to impart hydrophilic nature, it is also known in the art to coat the surfaces of the hydrophobic fibers with a surfactant or the like. However, when a large amount of liquid is applied, it washes the surfactant or the like away from the surfaces of the hydrophobic fibers to lower the hydrophilic nature of the fibers. Accordingly, a small amount of liquid remaining in the space between the hydrophobic fibers hardly moves toward the absorbent layer, and it still remains in that space.

On the other hand, the top layer mainly of cellulosic fibers in its entirety, as in Japanese Patent Laid-Open No. 24289/1996, gives a soft feel to the skin of a wearer, as its material is soft per se. When it has received a small amount of liquid or the sweat of a wearer, in addition, the cellulosic fibers retain the liquid, and, moreover, the small amount of liquid is well retained within the top layer owing to the hydrophilic capillary action of the fibers. Therefore, the liquid hardly returns to the skin of a wearer.

However, since the top layer of the type exhibits hydrophilic capillary action by itself, when a large amount of liquid is applied to the top layer, it does not rapidly move toward the absorbent layer, and it remains within the top layer. This results in a wet feel to the skin of a wearer.

In the top layer of a nonwoven fabric formed by mixing hydrophobic fibers and hydrophilic fibers as in Japanese Patent Laid-Open No. 10209/1979, the hydrophilic fibers are uniformly dispersed among the hydrophobic fibers. Accordingly, when a large amount of liquid is applied to the top layer and while it passes through the space between the hydrophobic fibers therein to move toward the absorbent layer, a part of the liquid is retained by the hydrophilic fibers and will therefore remain in the top layer. For this reason, the permeation rate of a large amount of liquid through the top layer is low.

SUMMARY OF THE INVENTION

An object of the present invention is to provide an absorbent article having a topsheet capable of smoothly passing a large amount of liquid therethrough and retaining a small amount of liquid therein so that it hardly gives a wet feel to the skin of a wearer to thereby improve a wear feel.

According to an aspect of the invention, there is provided an absorbent article comprising a topsheet, a backsheet and an absorbent core positioned between the topsheet and the backsheet, wherein;

the topsheet contains hydrophobic fibers and hydrophilic fibers shorter than the hydrophobic fibers, the hydrophobic fibers are thermally bonded to each other, at least a part of the hydrophilic fibers form aggregates that disperse in the sheet, and at least a part of the hydrophilic fibers that form the aggregates are bonded to the surfaces of the hydrophobic fibers.

In the above, preferably, the fiber density of the hydrophilic fibers that form the aggregates is higher than the fiber density of the area of the sheet not having the aggregates therein. More preferably, the fiber density of the hydrophilic fibers that form the aggregates falls between 1.5 times and 3 times the fiber density of the area of the sheet not having the aggregates therein.

When the topsheet is divided into two layers in the direction parallel to its thickness, one being a face layer that receives liquid and the other being a back layer adjacent to the absorbent core, it is desirable that the hydrophilic fiber aggregates are not in the face layer but are only in the back layer. Thus constituted, the hydrophilic fiber aggregates do not drop away from the face layer of the topsheet that receives liquid, and the surface strength of the liquid-receiving face layer of the topsheet can be high.

In the above, preferably, the basis weight of the topsheet falls between 20 and 60 $g/m^2$, and the basis weight of the face layer of the topsheet falls between 5 and 15 $g/m^2$. Thus constituted, the distance between the liquid-receiving surface of the face layer of the topsheet and the hydrophilic fiber aggregates existing in the back layer of the topsheet can be shortened, so that the liquid applied to the face layer of the topsheet can be readily absorbed by the hydrophilic fiber aggregates.

For example, the hydrophobic fibers have a fiber length of from 38 to 64 mm; and the hydrophilic fibers have a fiber length of from 5 to 25 mm. Preferably, the fiber length of the hydrophilic fibers is at most ½ of the fiber length of the hydrophobic fibers. If the fiber lengths are within the ranges, the hydrophilic fibers can be readily formed into the aggregates and dispersed among the hydrophobic fibers by using a conventional carding unit.

Preferably, the amount of the hydrophobic fibers in the topsheet falls between 70 and 98% by weight, and that of the hydrophilic fibers therein falls between 2 and 30% by weight. If the amount of the hydrophilic fibers in the topsheet is 30% by weight or less, more preferably 10% by weight or less, the hydrophilic fiber aggregates can be well dispersed in the sheet while suitably spaced from each other.

Preferably, the hydrophilic fibers are natural cellulose fibers having a modified cross section or a hollow cross section.

According to the invention, the topsheet is mainly formed by thermally bonding the hydrophobic fibers and the hydrophilic fibers aggregates having a higher density are dispersed therein. Therefore, when a large amount of liquid is applied to the topsheet, the liquid is drawn by the hydrophilic capillary action of the absorbent core and rapidly passes through the area of the sheet consisting essentially of hydrophobic fibers to be absorbed by the absorbent core.

When a small amount of liquid or the sweat of a wearer is applied to the topsheet, on the other hand, it is readily retained by the high-density, hydrophilic fiber aggregates dispersed in the topsheet owing to their hydrophilic capillary action. Accordingly, the small amount of liquid remains little in the space between the hydrophobic fibers in the topsheet, and returns little to the skin of the wearer. Therefore, the surface of the topsheet is well kept in a dry condition, and a wet feel is hardly given to the skin of a wearer.

DESCRIPTION OF THE PREFERRED EMBODIMENTS

Figure 1:
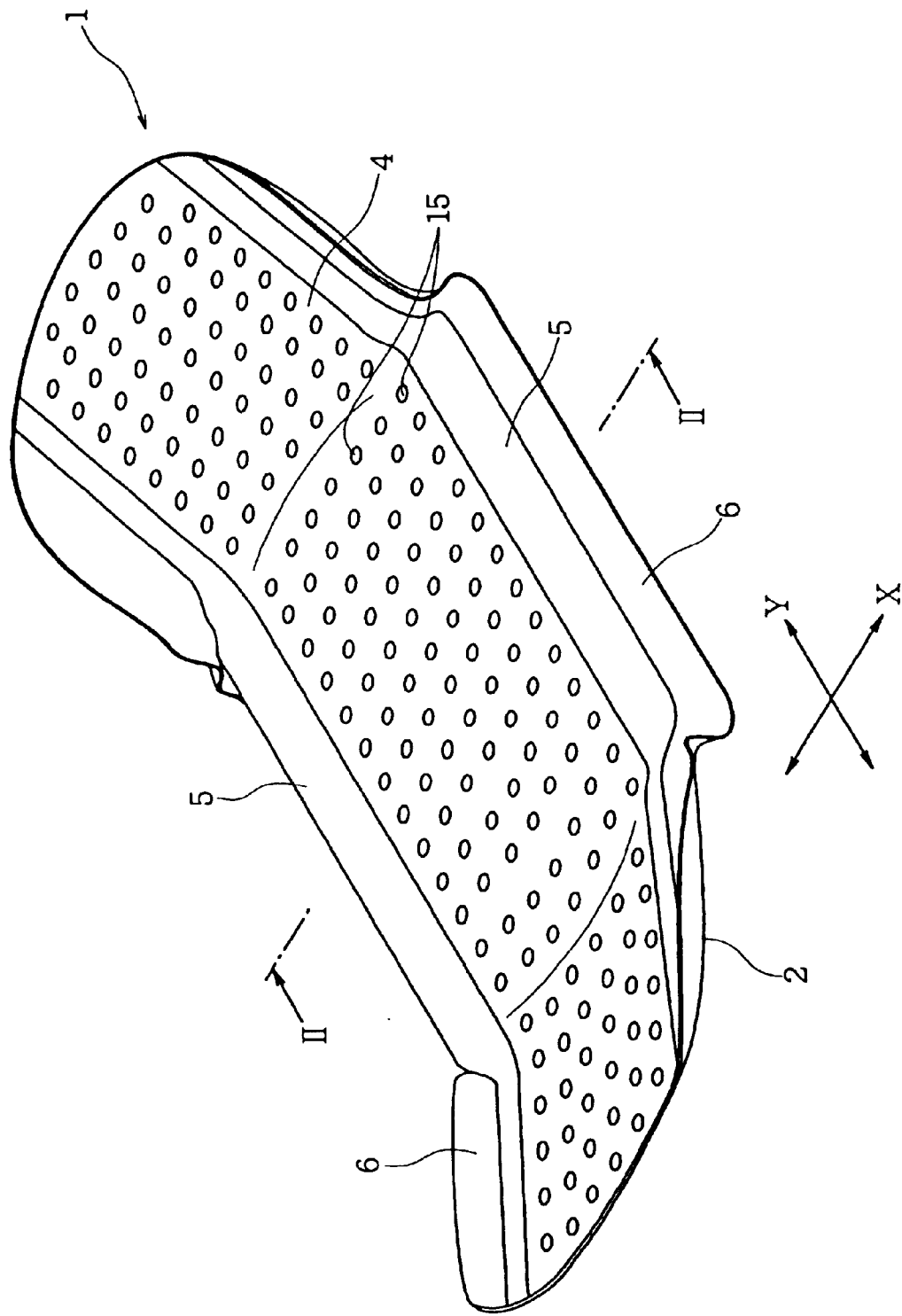
FIG. 1 is a perspective view of a sanitary napkin, one embodiment of the absorbent article of the invention.
Figure 2:
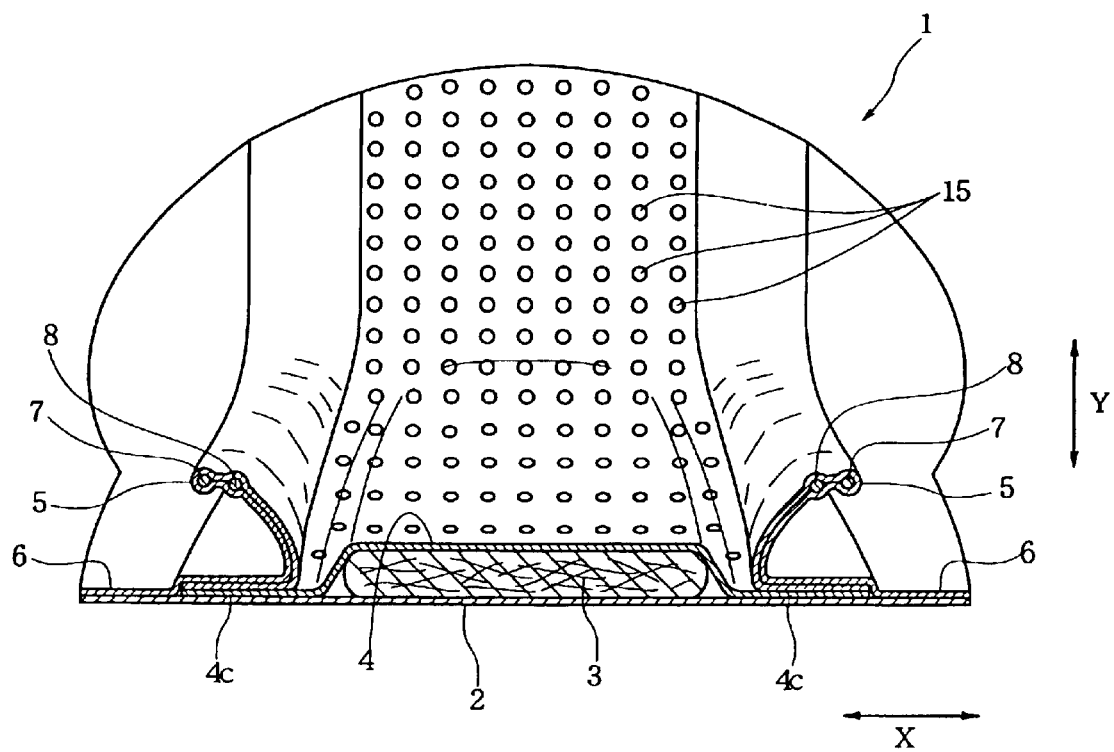
FIG. 2 is a cross-sectional view of the sanitary napkin of FIG. 1, cut along the line II—II.
Figure 3:
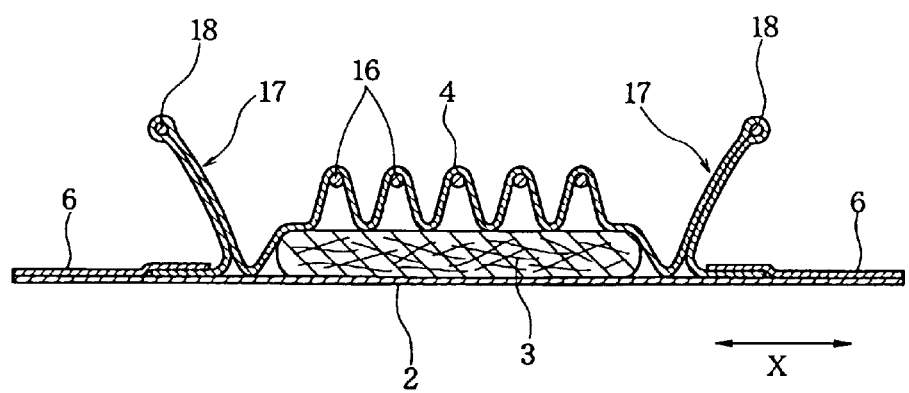
FIG. 3 is a cross-sectional view of another sanitary napkin.
Figure 4:
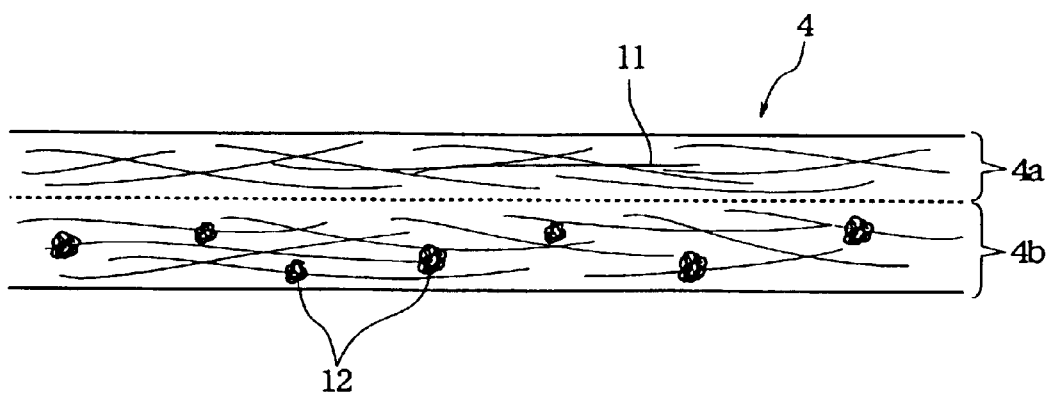
FIG. 4 is an enlarged schematic view showing a part of the cross section of a topsheet.
Figure 5:
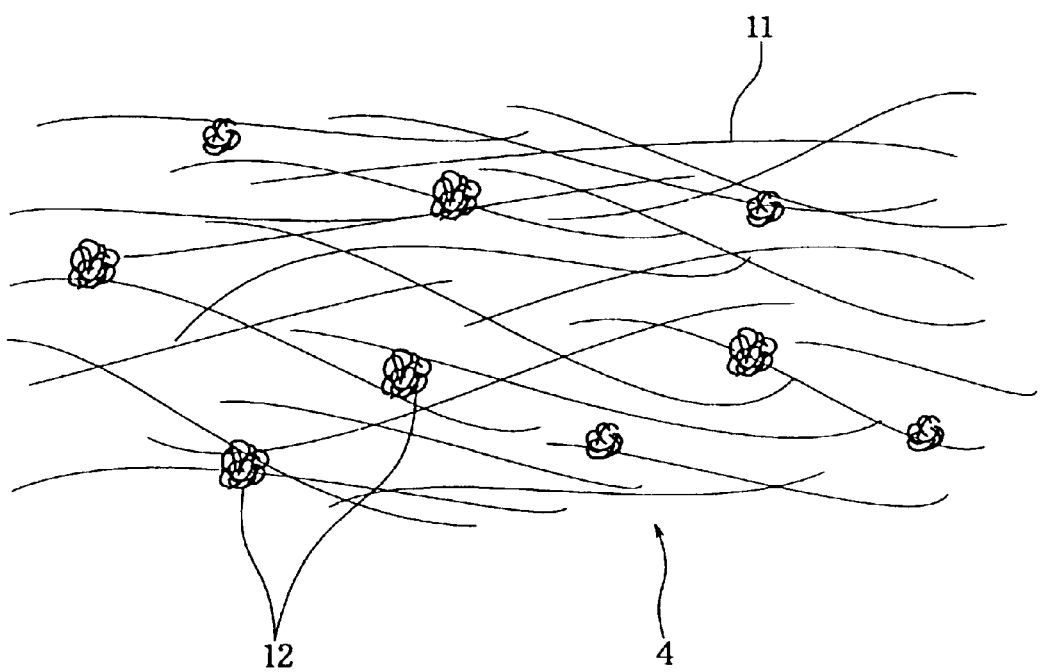
FIG. 5 is an enlarged schematic plan view showing a part of the topsheet of FIG. 4, seen from the back thereof.
Figure 6:
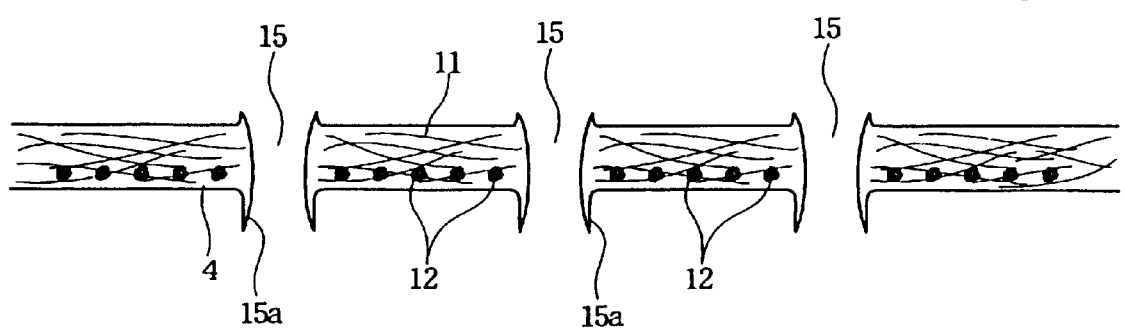
FIG. 6 is an enlarged cross-sectional view showing holes of the topsheet.
Figure 7:
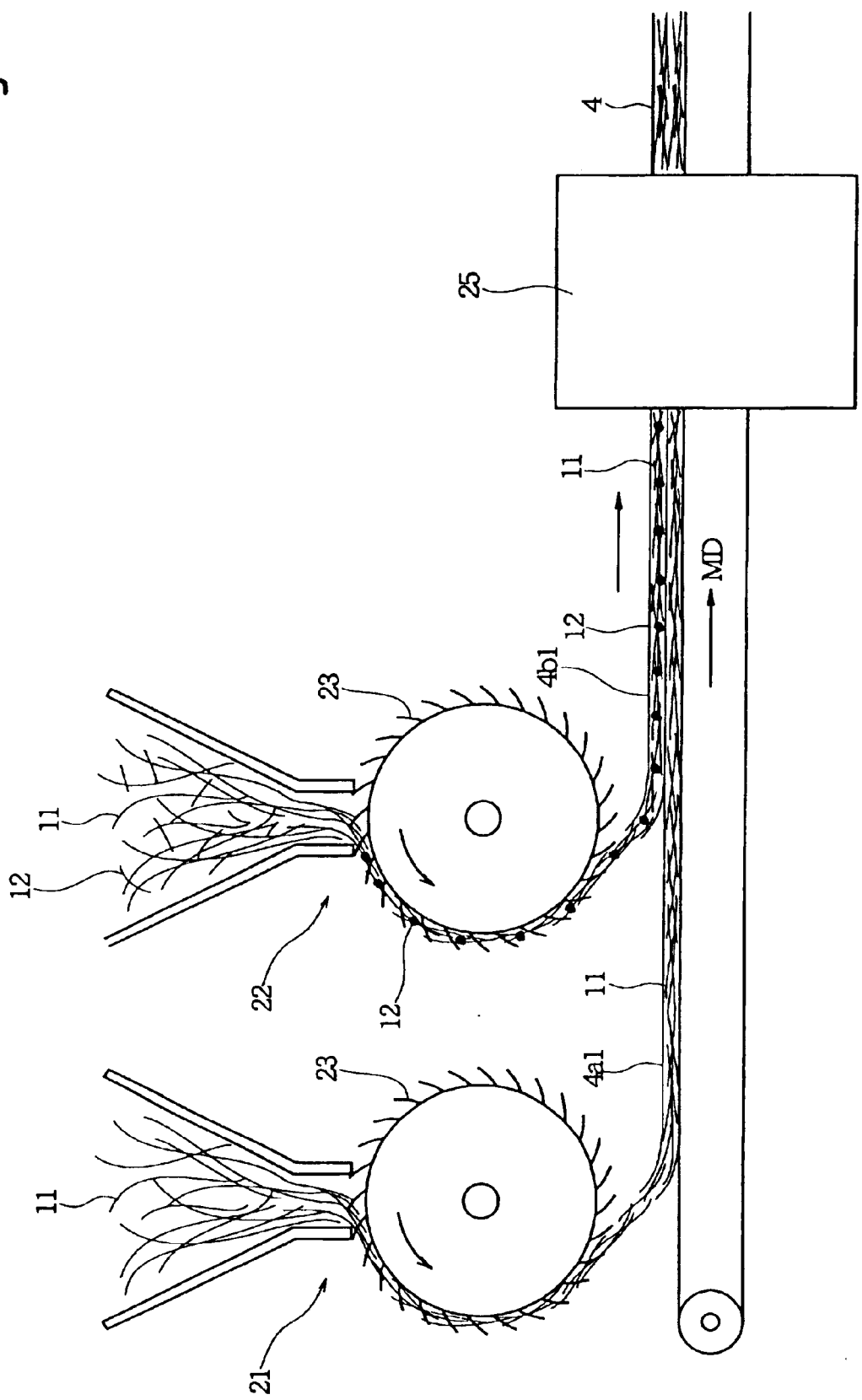
FIG. 7 is a schematic view showing a process of producing the topsheet of FIG. 4.
Figure 8A:
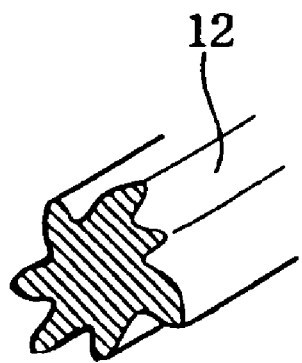
FIG. 8A and FIG. 8B are enlarged views showing the cross section of preferred profiles of hydrophilic fibers.
Figure 8B:
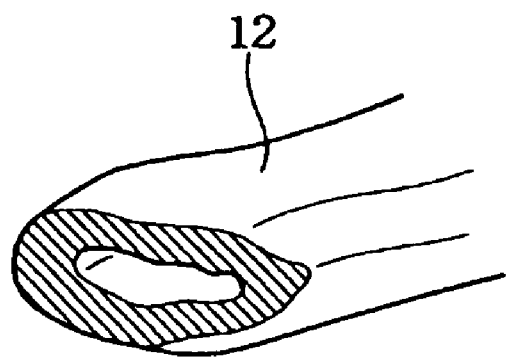

The invention will be described with reference to the accompanying drawings. FIG. 1 is a perspective view of a sanitary napkin 1, one embodiment of the absorbent article of the invention, seen from its liquid-receiving side; FIG. 2 is a cross-sectional view of FIG. 1, cut along the line II—II; FIG. 3 is a cross-sectional view of another sanitary napkin; FIG. 4 is an enlarged schematic view showing a part of the cross section of a topsheet of the sanitary napkin; FIG. 5 is an enlarged schematic plan view showing a part of the topsheet, seen from the back thereof; FIG. 6 is an enlarged cross-sectional view showing holes of the topsheet; FIG. 7 is a schematic view showing one example of a process of producing the topsheet of FIG. 4; and FIG. 8A and FIG. 8B are enlarged cross-sectional views showing preferred examples of hydrophilic fibers.

The sanitary napkin 1 of FIG. 1 and FIG. 2 comprises a main body including: a backsheet (or back layer) 2 that is intended to be placed adjacent to an external support such as undergarments; an absorbent core (or absorbent layer) 3 positioned nearly in the center of the transverse direction (direction X) of the napkin 1, which is intended to absorb body exudates; and a topsheet (or top layer) 4 that covers the liquid-receiving face of the absorbent core 3. The side portions 4c of the topsheet 4, lying opposite one another in the transverse direction (direction X), are joined to the surface of the backsheet 2 outwardly of the sides of the absorbent core 3.

At two sides of the main body of the sanitary napkin 1, lying opposite one another in the transverse direction (direction X), provided are a pair of leakage-preventive side walls 5, 5 both extending in the longitudinal direction (direction Y) of the napkin 1. In this embodiment, each leakage-preventive side wall 5 is formed of a single hydrophobic sheet 6.

The hydrophobic sheets 6 are joined onto the two sides of the main body, except for the portions forming the leakage-preventive side walls 5. The hydrophobic sheet 6 is joined not only to the backsheet 2 but also to the side portion 4c of the topsheet 4.

The hydrophobic sheet 6 is folded back at the top of the leakage-preventive side wall 5, and two elastic members 7, 8 are disposed between the two folded portions of the hydrophobic sheet 6. While stretched in the longitudinal direction (direction Y), the elastic members 7, 8 are joined to the hydrophobic sheet 6. Accordingly, when the sanitary napkin 1 is in a free condition, the hydrophobic sheet 6 receives elastic contraction forces in the longitudinal direction at the top of the leakage-preventive side wall 5.

At front and rear ends of the sanitary napkin 1, lying opposite one another in the longitudinal direction (direction Y), the hydrophobic sheet 6 forming the leakage-preventive side wall 5 is folded outward and fixed to the main body. The elastic contraction forces of the elastic members 7, 8 act on the top of each leakage-preventive side wall 5. Therefore, in a free condition, the sanitary napkin 1 is concavely curved in the longitudinal direction, and the leakage-preventive side walls 5, 5 stand up toward the skin of a wearer at two sides of the absorbent core 3.

As in the schematic views of FIG. 4 and FIG. 5, the topsheet 4 is made of a relatively bulky nonwoven fabric having therein many voids between fibers constituting it. The nonwoven fabric comprises hydrophobic synthetic fibers 11 and hydrophilic fiber aggregates 12. The hydrophobic synthetic fibers 11 have a fiber length of from 38 to 64 mm and a fineness of from 2.2 to 6.6 dtex. The hydrophilic fibers are natural cellulose fibers such as cotton and/or rayon fibers, and they have a fiber length of from 5 to 25 mm. Cotton is preferred for the hydrophilic fibers. The cotton fineness may fall between 1.2 and 11 dtex or so. In the topsheet 4, hydrophilic fibers not forming aggregates 12 may be dispersed among the hydrophobic fibers 11. Preferably, however, more than a half of the hydrophilic fibers in the topsheet 4 forms the aggregates 12.

The aforementioned hydrophilic fibers may have a modified cross section as in FIG. 8A, or may have a hollow cross section as in FIG. 8B; and they may be natural cellulose fibers of, for example, cotton. The modified cross-section fibers referred to herein are meant to indicate fibers not having a circular or oval cross section and not having a plain surface, or that is, fibers of which the surface is grooved or recessed. The hydrophilic fibers having such a modified cross section have a large surface area so that their ability to absorb and retain liquid is high. Natural cellulose fibers having fibrillated capillaries are also favorable for the topsheet 4 of the invention, as their ability to absorb and retain liquid is high.

The hydrophilic fibers having such a short fiber length as mentioned above are massed or crimped to form the aggregates 12 and are dispersed in the topsheet 4 to be held among the hydrophobic synthetic fibers 11, as shown in FIG. 4 and FIG. 5. The fiber density of the hydrophilic fiber aggregates 12 is higher than the fiber density of the hydrophobic synthetic fibers 11 in the area of the topsheet 4 not containing the hydrophilic fiber aggregates 12 therein and than the fiber density of the hydrophobic synthetic fibers 11 and the hydrophilic fibers not forming aggregates 12 in the area of the topsheet 4 not containing the hydrophilic fiber aggregates 12 therein but containing the hydrophilic fibers not forming aggregates 12 therein.

As used herein, the term "hydrophilic fiber aggregate" refers to hydrophilic fibers which are roundly massed or crimped to be entangled together so as to have a higher fiber density than the fiber density of the area of the topsheet not containing the aggregates therein.

Preferably, the density of the hydrophilic fiber aggregates 12 falls between 1.5 and 3 times the fiber density of the area not containing the aggregates 12 therein. For example, the density of the aggregates 12 is 0.03 g/cm$^3$; and the density of the area not containing the aggregates 12 falls between 0.05 and 0.09 g/cm$^3$.

At least the surface of the hydrophobic synthetic fibers 11 is made from a low-melting-point material. Preferably, the fibers 11 are core/sheath conjugated fibers of which the core is made from PP (polypropylene) or PET (polyethylene terephthalate) and the sheath is made from PE (polyethylene). The fibers 11 may also be PE fibers. However, for ensuring suitable voids in the topsheet 4 (nonwoven fabric), preferred are the above-mentioned, high-rigidity core/sheath conjugated fibers of which the core is made from PP or PET. If desired, the hydrophobic synthetic fibers 11 may be coated with a surfactant so as to make them hydrophilic. However, if the thus-hydrophilicated fibers receive a large amount of liquid, the surfactant around them will be washed away and the fibers could not be hydrophilic. Even in that condition, fine liquid drops having penetrated into the topsheet 4 of the absorbent article of the invention can be well absorbed by the hydrophilic fiber aggregates 12 existing in the topsheet 4.

Preferably, the hydrophobic synthetic fibers 11 contain titanium oxide therein and are opaque and milky. When the hydrophobic synthetic fibers 11 contain from 0.5 to 10% by weight of titanium oxide, the topsheet 4 can be opaque and milk and it can mask the color of blood absorbed by the absorbent core 3 below it.

The topsheet 4 is made of a thermal-bonded nonwoven fabric which is preferably prepared in a through-air bonding process. In this, the hydrophobic synthetic fibers 11 are thermally bonded to each other, and the hydrophilic fiber aggregates 12 of, for example, cotton are secured to the surfaces of the hydrophobic synthetic fibers 11, as the surfaces exhibit fusion bonding force in molten or semi-molten condition.

In order that the hydrophilic fiber aggregates 12 can be surely held by the hydrophobic synthetic fibers 11 in the topsheet 4, it is desirable that the hydrophobic synthetic fibers 11 are long to some degree and that the sheet structure of the topsheet 4 ensures good bonding of the hydrophilic fiber aggregates 12 to the surfaces of the hydrophobic synthetic fibers 11. For example, in a point-bonded nonwoven fabric comprising heat-fusible short fibers, the hydrophilic fiber aggregates 12 could not be surely held among the hydrophobic fibers 11 and will easily drop off. A spun-laced nonwoven fabric in which the fibers are entangled by the action of water jets, and a chemical-bonded nonwoven fabric in which the fibers are chemically bonded to each other are not bulky and their porosity is low, so that a large amount of liquid given thereto is difficult to penetrate through the space between the hydrophobic synthetic fibers to run toward absorbent core 3. For these reasons, therefore, a thermal-bonded nonwoven fabric prepared in a through-air bonding process is preferred for the topsheet 4, as so mentioned hereinabove. The thermal-bonded nonwoven fabric for the topsheet 4 may be heated with a heat roller instead of hot air; or a spun-bonded nonwoven fabric comprising heat-fusible long fibers may also be used for the topsheet 4.

As so mentioned hereinabove, the topsheet 4 preferably has a suitable degree of porosity in order that a large amount of liquid may pass through the space between the hydrophobic synthetic fibers 11 therein to run toward the absorbent core 3 below the topsheet 4. Therefore, it is desirable that the basis weight of the topsheet 4 falls between 20 and 60 g/m$^2$ and the thickness (bulkiness) thereof falls between 0.3 and 10 mm, more preferably between 0.3 and 2 mm. Having the basis weight and the thickness falling within the defined ranges, the topsheet 4 is good as a large amount of liquid given thereto can smoothly penetrate through the space between the hydrophobic synthetic fibers 11 therein to run toward the absorbent core 3 below the topsheet 4.

In order to facilitate good penetration of a large amount of liquid through the space between the hydrophobic synthetic fibers 11 constituting the topsheet 4 to reach the absorbent core 3, it is desirable that the hydrophilic fiber aggregates 12 in the topsheet 4 are appropriately dispersed around the hydrophobic synthetic fibers 11 therein. It is also desirable that the hydrophobic synthetic fibers 11 account for from 7.0 to 98% by weight of the topsheet 4, and the hydrophilic fibers having formed the aggregates 12 and those not having formed them account for, in total, from 2 to 30% by weight, more preferably from 2 to 10% by weight of the topsheet 4.

Preferably, the hydrophilic fiber aggregates 12 are uniformly dispersed in the topsheet 4 (nonwoven fabric), while suitably spaced from each other. The hydrophilic fiber aggregates 12 may be uniformly distributed throughout the topsheet 4 from the face to the back thereof. Preferably, however, the hydrophilic fiber aggregates 12 do not exist in the liquid-receiving surface of the topsheet 4. In the embodiment of FIG. 4, the topsheet 4 is divided at the mid-portion of its thickness into upper and lower portions, the upper portion being a face layer 4a that receives liquid and the lower portion being a back layer 4b adjacent to the absorbent core 3. In this, the hydrophilic fiber aggregates 12 are not in the face layer 4a but are dispersed in the back layer 4b.

If the hydrophilic fiber aggregates 12 are in the liquid-receiving face layer 4a of the topsheet 4, the surface strength of the liquid-receiving surface of the topsheet 4 lowers, and, in addition, the hydrophilic fiber aggregates 12 will drop off from the topsheet 4 to the side of the wearer. Moreover, the hydrophilic fiber aggregates 12 existing in the face layer 4a of the topsheet 4 will retain water and the retained water is easily given to the skin of a wearer.

In case where the topsheet 4 is composed of the two layers (the face layer 4a consisting essentially of the hydrophobic synthetic fibers 11 and the back layer 4b containing the hydrophilic fiber aggregates 12 dispersed therein) as shown in FIG. 4, and when the basis weight of the face layer 4a is too large, then the liquid-receiving surface of the topsheet 4 will be too remote from the hydrophilic fiber aggregates 12 existing only in the back layer 4b. If so, a small amount of liquid applied to the face layer 4a could not be well retained by the hydrophilic fiber aggregates 12 and will return to the skin of a wearer. In that condition, the effect of the topsheet 4 to prevent the skin of a wearer from being wetted will be lowered. Therefore, it is desirable that the basis weight of the face layer 4a falls between 5 and 15 g/m².

Hydrophilic fibers not forming the aggregates 12 may be dispersed in the face layer 4a of the topsheet 4.

The topsheet 4 thus far described is highly permeable to liquid, and its surface is well kept dry. Therefore, the nonwoven fabric of FIG. 4 may be directly used for the topsheet of the absorbent article such as the sanitary napkin 1 of the invention. Preferably, however, the nonwoven fabric of FIG. 4 is further formed with a large number of holes 15, as shown in FIGS. 1 and 2 and in the cross section of FIG. 6. With the holes 15 formed through it, the topsheet 4 has capillaries that open onto the absorbent core 3, and a large amount of liquid passes through the holes 15 of the topsheet 4 and is readily absorbed by the absorbent core 3.

The topsheet 4 is preferably needled to form the holes 15 through it in such a manner that the fibers 15a constituting the inner surface of each hole 15 protrude toward the absorbent core 3, as shown in FIG. 6. With the holes 15 formed in that manner, the topsheet 4 can be more bulky and its wearer's surface is prevented from being fluffy. Preferably, the pore diameter of each hole 15 falls between 0.3 and 20 mm, and the area of the pores 15 in the topsheet 4 falls between 5 and 60%. If the pore diameter and the pore area are smaller than the defined ranges, the liquid permeability of the topsheet 4 will be poor; but if larger than them, the phenomenon referred to as "wet back", in which the liquid having been once absorbed by the absorbent core 3 returns to the topsheet 4, will occur to wet the skin of a wearer.

The backsheet 2 of the sanitary napkin 1 is made of a liquid-impermeable sheet. For this liquid-impermeable backsheet 2, usable is any of an air-permeable (breathable). resin film, a spun-bonded or spun-laced nonwoven fabric specifically processed for water repellency, and a nonwoven fabric of which the back is laminated with an air-permeable resin film. Preferably, an adhesive layer is disposed on the back of the backsheet 2, via which the sanitary napkin 1 is secured on an external support such as an undergarment; and the adhesive layer is preferably coated with a released paper (or separate paper) that protects it until use of the sanitary napkin 1.

The absorbent core 3 is made from ground pulp or from a mixture of ground pulp and a highly absorbent polymer. Concretely, ground pulp or a mixture of ground pulp and a highly absorbent polymer is wrapped with an absorbent sheet such as tissue paper.

The hydrophobic sheet 6 to form the leakage-preventive side wall 5 is hydrophobic or repellent to water, and it may be made of a melt-blown nonwoven fabric, a through-air-bonded nonwoven fabric, a point-bonded nonwoven fabric, an air-laid nonwoven fabric, or a composite laminate of a spun-bonded nonwoven fabric and a melt-blown nonwoven fabric. It may also be made of a resin film, or a laminate of a nonwoven fabric and a resin film.

The liquid-permeable function of the topsheet 4 of the sanitary napkin 1 is described below.

As has been described heretofore, the topsheet 4 is made of a nonwoven fabric mainly of the hydrophobic synthetic fibers 11 and having a relatively high porosity. In the nonwoven fabric to form the topsheet 4, the hydrophilic fiber aggregates 12 are dispersed. Therefore, when the topsheet 4 has received a large amount of liquid such as menses, the large amount of liquid penetrates through the topsheet 4 and then reaches the absorbent core 3 below the topsheet 4. In this stage, the absorbent core 3 draws and absorbs the large amount of liquid owing to its hydrophilic capillary action. The surfaces of the hydrophobic synthetic fibers 11 in the topsheet 4 are poorly resistant to the liquid penetration through the topsheet 4, and therefore the liquid can rapidly pass through the space between the hydrophobic synthetic fibers 11 in the topsheet 4 and is then absorbed by the absorbent core 3. In the topsheet 4, the aggregates 12 are dispersed, while spaced from each other, and the liquid passes through the space between the hydrophobic synthetic fibers 11 in the area not containing the aggregates 12, and is rapidly absorbed by the absorbent core 3.

In the embodiment of the topsheet 4 illustrated in FIG. 6, the inner wall of each hole 15 consists essentially of hydrophobic synthetic fibers 11. In this, therefore, the liquid passing through the holes 15 is rapidly absorbed by the absorbent core 3 below the topsheet 4.

In case where a large amount of liquid passes through the topsheet 4, the hydrophilic fiber aggregates 12 dispersed in the topsheet 4 will receive a part of the liquid. In this case, however, the greater part of the liquid is drawn by the absorbent core 3 owing to the hydrophilic capillary action of the absorbent core 3, and only a small part of the liquid will be absorbed by the hydrophilic fiber aggregates 12. In addition, since the hydrophilic fiber aggregates 12 have a higher fiber density than that of the area not containing them in the topsheet 4, the small part of the liquid absorbed by the hydrophilic fiber aggregates 12 are well retained therein, not returning to the surface of the topsheet 4. In particular, in the embodiment of the topsheet 4 illustrated in FIG. 4, the hydrophilic fiber aggregates 12 are in the back layer 4b and are not in the face layer 4a. Therefore, the surface of the topsheet 4 of this embodiment is kept in a dry condition, and hardly wets the skin of a wearer.

On the other hand, in case where an extremely small amount of liquid is applied to the topsheet 4, or in case where a little sweat is given thereto from the skin of a wearer, or in case where the humidity inside the topsheet 4 has increased owing to the body temperature and the sweat of a wearer, the moisture is drawn and retained by the hydrophilic fiber aggregates 12 dispersed in the topsheet 4. Since the hydrophilic fiber aggregates 12 have a higher density than that of the area not containing them in the topsheet 4 and are dispersed in the topsheet 4, a small amount of water or water vapor existing inside the topsheet 4 is readily drawn by the hydrophilic fiber aggregates 12, and the thus drawn water is well retained in the aggregates 12. In addition, since the hydrophilic fiber aggregates 12 are remote from the surface of the topsheet 4, the liquid or the water thus retained in the aggregates 12 hardly returns to the surface of the topsheet 4.

Accordingly, the surface of the topsheet 4 is kept in a dry condition, not having a wet feel, and the wearer is free from a hot and stuffy feel.

The topsheet 4 may apply to a different type of sanitary napkin, as in FIG. 3 showing a cross-sectional view of a different sanitary napkin.

In the sanitary napkin illustrated in FIG. 3, the topsheet 4 is corrugated on the absorbent core 3, alternating hills and valleys in the transverse direction (direction X). At the top of each hill of the corrugated topsheet 4, provided is an elastic member 16 extending in the longitudinal direction (direction Y). While stretched in the longitudinal direction, the elastic member 16 is joined to the topsheet 4. Accordingly, the top of each hill is spaced from the absorbent core 3 owing to the elastic contraction force of the elastic member 16, and the hills of the topsheet 4 stand away from the absorbent core 3. Thus constituted, the substantial bulk of the topsheet 4 increases.

The height of the hills of the topsheet 4 preferably falls between 0.5 and 5 mm, and the hill pitch (i.e., the array pitch of hills of corrugations) in the transverse direction preferably falls between 0.5 and 10 mm.

If desired, as shown in FIG. 3, two sides of the topsheet 4, lying opposite one another in the transverse direction, may stand away from the backsheet 2, and elastic members 18 extending in the longitudinal direction may be attached to the top ends of the thus standing portions of the topsheet 4 to thereby form side walls 17. In this embodiment, the sanitary napkin is provided with hydrophobic sheets 6 on its surface at both the right and left sides adjacent to the side walls 17.

FIG. 7 shows one example of producing the topsheet 4 of FIG. 4 and FIG. 5.

In the process of FIG. 7, hydrophobic synthetic fibers 11 having a fiber length of from 38 to 64 mm are fed into the first-stage carding unit 21, and are opened by the pins 23 standing around the rotary roll therein. Since the hydrophobic synthetic fibers 11 are satisfactorily longer than the pitch of the pins 23 in the circumferential direction of the roll, they are carded in the machine direction (MD) and are then formed into a fibrous web 4a1 that is intended to form the face layer 4a of the topsheet 4.

Hydrophobic synthetic fibers 11 having a fiber length of from 38 to 64 mm and hydrophilic fibers (cotton) having a fiber length of from 5 to 25 mm are fed into the second-stage carding unit 22, and they are opened by the pins 23 standing around the rotary roll therein. Since the hydrophobic synthetic fibers 11 are long and tough (i.e., have a high rigidity), they are carded in MD owing to the opening force of the pins 23. On the other hand, the hydrophilic fibers are short, and especially those of cotton are not tough but flexible. Therefore, when they have received the opening force of the pins 23, they are not carded in MD. Most of them are massed or crimped to form aggregates 12, and are held between the adjacent pins 23, 23. As a result, the hydrophilic fiber aggregates 12 are dispersed in the space between the hydrophobic synthetic fibers 11 that have been carded in MD, and they form a fibrous web 4b1.

The fibrous web 4b1 is laminated over the fibrous web 4a1, and the resulting laminate is led into a through-air bonding hot chamber 25. In this hot chamber 25, the hydrophobic synthetic fibers 11 in the fibrous webs are thermally bonded, and the hydrophilic fiber aggregates 12 are secured to the fused surfaces of the hydrophobic synthetic fibers 11. Through the process, a nonwoven fabric to form the topsheet 4 is produced.

In place of the hot chamber 25, a hot roller may be used for thermally bonding the hydrophobic synthetic fibers 11 in the fibrous webs.

The nonwoven fabric thus produced through the process is composed of a face layer 4a that consists essentially of the hydrophobic synthetic fibers 11 and a back layer 4b that contains the hydrophilic fiber aggregates 12 dispersed around the hydrophobic synthetic fibers 11, as in FIG. 4.

Of course, only the second-stage carding unit 22 in the process of FIG. 7 may be used to form a single layer nonwoven fabric to be formed into the topsheet 4. This single layer nonwoven fabric comprises the hydrophobic synthetic fibers 11 and contains the hydrophilic fiber aggregates 12 dispersed around the fibers 11. In this case, it is desirable that the single layer nonwoven fabric produced is heated by pressing its surface against a hot roll or the like to thereby increase the fusion bonding strength of the fibers in the surface of the nonwoven fabric. This is for preventing the hydrophilic fiber aggregates 12 from dropping away from the surface of the nonwoven fabric.

In the absorbent article of the invention described in detail hereinabove, the topsheet having received a large amount of liquid rapidly passes the liquid through it, and the absorbent core below the topsheet absorbs the liquid. When a small amount of liquid or the sweat of a wearer is given to the topsheet, on the other hand, the hydrophilic fiber aggregates dispersed in the topsheet can retain the moisture to thereby keep the surface of the topsheet in a dry condition, not having a wet feel. Therefore, while it is worn, the absorbent article gives a comfortable feel to the wearer.

Although various exemplary embodiments have been shown and described, the invention is not limited to the embodiments shown. Therefore, the scope of the invention is intended to be limited solely by the scope of the claims that follow.

What is claimed is:

1. An absorbent article comprising a topsheet, a backsheet and an absorbent core positioned between the topsheet and the backsheet, wherein;

the topsheet contains hydrophobic synthetic fibers and hydrophilic fibers shorter than the hydrophobic fibers, the hydrophobic fibers are thermally bonded to each other, and at least a part of the hydrophilic fibers are formed into aggregates, wherein the aggregates are separate from each other and are uniformly dispersed in the topsheet, and are bonded to surfaces of the hydrophobic synthetic fibers.

2. The absorbent article asset forth in claim 1, wherein a fiber density of the aggregates is higher than a fiber density of a portion of the topsheet without the aggregates.

3. The absorbent article asset forth in claim 2, wherein the fiber density of the aggregates is 1.5 to 3 times the fiber density of the portion of the topsheet without the aggregates.

4. The absorbent article as set forth in claim 1, wherein the topsheet is so constituted that, when it is divided into two layers in the direction parallel to its thickness, one being a face layer that receives liquid and the other being a back layer adjacent to the absorbent core, the hydrophilic fiber aggregates are not in the face layer but are only in the back layer.

5. The absorbent article as set forth in claim 4, wherein the basis weight of the topsheet falls between 20 and 60 g/m$^2$, and the basis weight of the face layer of the topsheet falls between 5 and 15 g/m$^2$.

6. The absorbent article as set forth in claim 1, wherein the hydrophobic fibers have a fiber length of from 38 to 64 mm, and the hydrophilic fibers have a fiber length of from 5 to 25 mm.

7. The absorbent article asset forth in claim 1, wherein the topsheet is a thermally bonded nonwoven fabric containing the hydrophobic synthetic fibers in a range of 70 to 98 percent by weight and at least 50 percent of the hydrophillic fibers are formed into the aggregates.

8. The absorbent article as set forth in claim 1, wherein the hydrophilic fibers are natural cellulose fibers having a modified cross section or a hollow cross section.

* * * * *